United States Patent [19]

Frigerio et al.

[11] Patent Number: 4,921,848
[45] Date of Patent: May 1, 1990

[54] BILIARY ACID DERIVATIVES, PROCESSES FOR THE PREPARATION THEREOF AND PHARMACEUTICAL COMPOSITIONS CONTAINING THEM

[75] Inventors: Giuliano Frigerio, Milan; Roberto Pellicciari, Perugia; Aldo Roda, Bologna, all of Italy

[73] Assignee: Gipharmex S.P.A., Milan, Italy

[21] Appl. No.: 259,870

[22] Filed: Oct. 19, 1988

[30] Foreign Application Priority Data

Oct. 20, 1987 [IT] Italy ................. 22343 A/87

[51] Int. Cl.$^5$ ........................... A61K 31/56; C07J 1/00
[52] U.S. Cl. ..................... 514/182; 552/549; 552/550; 552/551
[58] Field of Search ....................... 260/397.1; 514/182

[56] References Cited

U.S. PATENT DOCUMENTS

| | | | |
|---|---|---|---|
| 2,615,902 | 10/1950 | Hirschmann et al. | 260/397.1 |
| 2,938,031 | 4/1960 | Bible et al. | 260/397.1 |
| 2,966,499 | 12/1960 | Hinkley et al. | 260/397.1 |
| 3,591,687 | 7/1971 | Bray | 514/182 |
| 4,172,076 | 10/1979 | Hirsch et al. | 260/397.1 |

Primary Examiner—Joseph A. Lipovsky
Attorney, Agent, or Firm—Bucknam and Archer

[57] ABSTRACT

Compounds of formula I

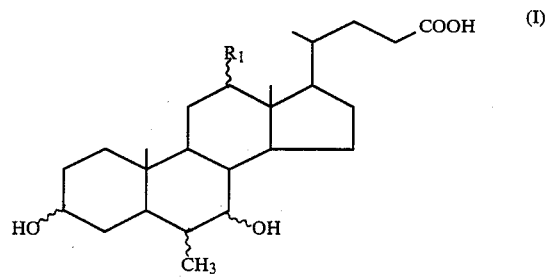

wherein:
$R_1$ is hydrogen or hydroxy, and the methyl and hydroxy groups at 6- and 7-positions respectively can be either in $\alpha$ or $\beta$ configuration, are useful in human therapy. Compounds I are prepared by methylation of the corresponding appropriately protected 7-keto-derivatives.

5 Claims, No Drawings

BILIARY ACID DERIVATIVES, PROCESSES FOR THE PREPARATION THEREOF AND PHARMACEUTICAL COMPOSITIONS CONTAINING THEM

The present invention relates to biliary acid derivatives, to a process for the preparation thereof and to pharmaceutical compositions containing them.

The derivatives of the present invention have the following general formula I

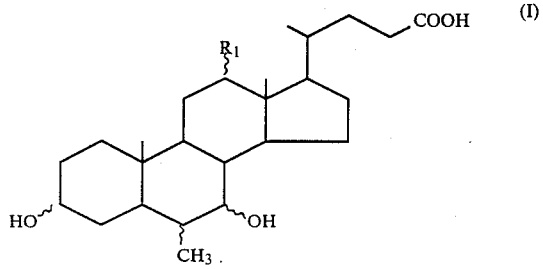

wherein $R_1$ is hydrogen or hydroxy, and the methyl and hydroxy groups at 6- and 7-positions respectively can be either in $\alpha$ or $\beta$ configuration.

In other words, compounds I are the 6-methyl derivatives of the following natural biliary acids: ursodeoxycholic (UDCA) ($3\alpha, 7\beta$ OH), ursocholic ($3\alpha, 7\beta$ OH; $R_1$=OH), chenodeoxycholic ($3\alpha, 7\alpha$OH) and cholic ($3\alpha, 7\alpha$OH; $R_1$=OH) acids.

The present invention also relates to the physiologically acceptable salts of compounds of formula I, as well as possible glycine or taurine conjugated forms. Moreover, since compounds I can have the methyl group at 6-position as well as the hydroxy group at 7-position either in $\alpha$ or $\beta$ configurations, the invention also relates to the single isomers or diastereoisomers and the mixtures thereof.

The above cited biliary acids have been used for a long time in human therapy for the treatment of biliary calculosis, as antidyspeptic, eupeptic, antidyslipidemic and choleretic agents, and generally in all those pathological conditions in which a stimulation of biliary flow and a qualitative and/or quantitative change thereof are required.

Therapeutic possibilities of natural molecules promoted the development of a number of synthetic or semi-synthetic derivatives in the attempt to obtain improved drugs as regard pharmacokinetic, metabolism or chemico-physical aspects (lipophilia/hydrophilia ratio, stability, critical micellar concentration). See, for instance, EP-A 83106708.7, 84104598.2, 84109811.4, 85115611.7 and U.S. Pat. Nos. 4648995, 4460509, 4545938.

The above cited U.S. patents particularly disclose 7-methyl, 7-hydroxy derivatives which, in comparison with the natural moleculae, should provide the advantage of a higher resistance to intestinal bacterial flora, and accordingly a prolonged half-life as well as an increase in stability.

These and other advantages are provided by the compounds of the present invention, which compounds are characterized by the presence of a methyl group at 6-position, 7-position being substantially unchanged in comparison with the natural molecula, which is per se advantageous since 7-position has been found to be critical as regard pharmacological activity.

The methyl group at the 6-position makes the molecule more hydrophobic and more liable to form micells; this is for example the case of UDCA 6-methyl derivative with respect to UDCA itself.

In vitro tests carried out by incubating compounds I with human feces under aerobic conditions, in comparison with UDCA, proved that compounds I have a higher stability and a lower deoxylation rate than UDCA, and that the half-lives for compounds I and UDCA are respectively of >24 hours and 8 hours.

Tests effected in rats by intravenous administration of the compounds of the invention at the dose of 2 $\mu$mol/min/Kg body weight evidenced a choleretic effect comparable to that of UDCA and an efficient recovery of the compound in bile. The recovered chemical products are mainly tauro-conjugated forms, and glyco-conjugated forms in a minor part, in a ratio smaller to that of UDCA.

As regards the effect on lipidic biliary secretion, compounds I preferentially decrease cholesterol secretion, keeping constant the phospholipid one.

The compounds of the invention, for the envisaged therapeutical uses, are administered in form of pharmaceutical compositions prepred according to known techniques and excipients, as described e.g. in "Remington's Pharmaceutical Sciences Handbook", Hack Pub. Co., N.Y. USA.

The preferred administration route is the oral one, and the daily doses, which will vary depending on the pathology to be treated and the patient's conditions, will in principle be comprised from 50 to 500 mg, one or more times a day.

Examples of suitable pharmaceutical compositions comprise capsules, tablets, dragees, sugar-coated pills, syrups, granulates, solutions, vials. The compounds of the invention can also be administered by local perfusion, before or after surgical operations, in form of dispersible solutions or powders.

The process for the preparation of compounds I consists in the methylation, under controlled conditions, of the compounds of general formula II

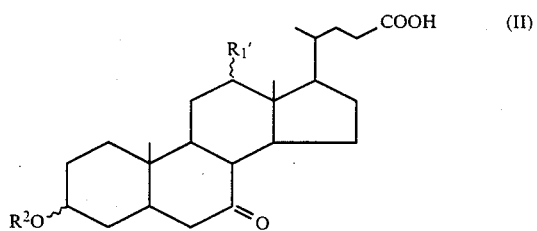

in which $R_2$ is an hydroxy-protecting group and $R'_1$ is hydrogen or an hydroxy-protected group.

Methylation is carried out using a methyl halide and appropriate base-solvent systems able to promote the kinetic control in enolate formation.

Lithium dialkylamides deriving from secondary amines such as diethylamine, diisopropylamine, piperidine, isopropylcyclohexylamine, hexamethylenedisilazine, etc. can be used as the bases in the present invention. Particularly preferred are lithium diisopropylamine or isopropylcyclohexylamine.

Suited solvents are 1,2-dimethoxyethane, tetrahydrofuran, ethyl ether, preferably in the presence of hexamethylphosphoramide (HMPA).

The reaction temperature is lower than −50° C., preferably about −78° C.

Resulting compounds III

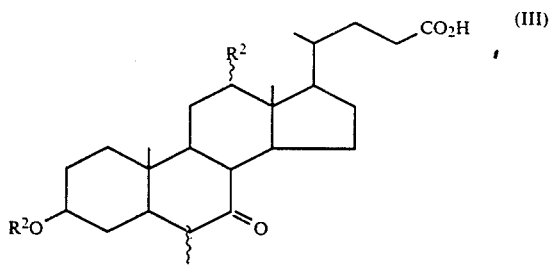

are then freed from the protecting groups and keto group at 7-position is reduced to 7-hydroxy group.

Any group stable under the reaction conditions can be used as the protecting group. Particularly preferred is the tetrahydropyranyl group. Reduction of keto group can finally be effected by means of conventional reactions, e.g. with metal hydrides or according to Meerwein-Ponndorf.

In case compound III is impure for the presence of unreacted compound II, it is advisable to carry out a chromatographic separation on the methyl ester mixture.

The following non-limiting example illustrates the invention in more detail.

EXAMPLE (a) 3-α-tetrahydropyranyloxy 7-keto-5-β-cholan-24-oic acid (II)

P-toluenesulfonic acid (3.00 g, 1.6 mmol) then, slowly, 3,4-dihydro-2H-pyran (DHP) (2.3 g, 27 mmol) were added to a solution of 3-α-hydroxy-7-keto-5-β-cholan-24-oic acid (3.00 g. 7.68 mmol) in anhydrous dioxane (55 ml). The reaction mixture was left under magnetic stirring for 15 minutes at room temperature, then it was added with methanol saturated with $NH_3$ to pH 8–9. The mixture was evaporated under vacuum, the residue was taken up into chloroform and washed with a saturated $NaHCO_3$ solution (2×20 ml). After drying over anhydrous magnesium sulfate and evaporation under vacuum, the residue (3.5 g) was chromatographed on $SiO_2$ (φ 4, h 14). By elution with 95:5 $CHCl_3$/MeOH polymerization products of dihydropyran were obtained, then by elution with 90:10 $CHCl_3$/MeOH the desired compound I was obtained (2.7 g), 72% yield.

H-NMR ($CDCl_3$) δ: 0.68 (s, C-18 Me, 3H); 0.9 (d, C-21 Me, 3H); 1.17 (s, C-19 Me, 3H); 3.3–4.0 (2 m, C-2' CH, C-6' $CH_2$, 3H); 4.6–4.8 (brs, C-3 CH-OH, 1H).

(b) 3-α-tetrahydropyranyloxy-6-ξ-methyl-7-keto-5-β-cholan-24-oic acid (III)

N-butyl lithium (9.25 ml, 1.6M solution in hexane), then HMPA (2.5 g, 14 mmol) were added to a diisopropylamine solution (1.41 g, 14 mmol) in tetrahydrofuran (THF) (50 ml). The system was cooled to −78° C. and acid II (2.00 g, 4 mmol) in THF (20 ml) was slowly added. 5 Minutes after the end of the addition, methyl iodide (17.1 g, 12 mmol) was added dropwise. The reaction mixture was then left to warm to room temperature, then it was acidified with 10% HCl and extracted with chloroform (3×20 ml). The combined organic phases were washed with water, dried over sodium sulfate and evaporated under vacuum. The crude compound (2.00 g) was chromatographed on $SiO_2$ (φ 4, 12 hours). By elution with 98:2 $CHCl_3$/MeOH, 1.95 g of a mixture of the starting compound II and the methyl derivative III was obtained.

(c) Separation of methyl 3-α-hydroxy-6-ξ-methyl-7-keto-5-β-cholanoate

The mixture of II and II (g 2.52, mmol 5.12) obtained in (b) was dissolved in THF (4 ml), added with some drops of 37% HCl and stirred for 30 minutes at room temperature; then it was poured into water and extracted with chloroform (2×25 ml). The combined organic portions were dried over anhydrous sodium sulfate and evaporated under reduced pressure. 2.00 g of a mixture consisting of the starting compound and deprotected compound III were obtained. The mixture was dissolved in methanol (200 ml) and p-toluenesulfonic acid (0.400 g) was added to the resulting solution. After slow magnetic stirring at room temperature for 12 hours, solvent was evaporated off under vacuum, the residue was taken up into chloroform and washed with water (2×20 ml). The organic phases were dried over anhydrous sodium sulfate and the crude product was flash chromatographed on $SiO_2$ (φ 5, 20 h). By elution with chloroform, 1.00 g (50%) of the title compound was obtained. H-NMR ($CDCl_3$) δ: 0.68 (s, C-18 Me 3H); 0.9 (d, C-21 Me, 3H); 1.17 (s, C-19 Me, 3H); 3.6 (s, $CO_2$ $CH_3$, 3H) and 0.98 g of VI (49%).

(d) 3-α-hydroxy-6-ξ-methyl-7-keto-5-β-cholan-24-oic acid The ester obtained in (c) (0.900 g, 2.1 mmol) was refluxed for 3 hours in a 10% KOH solution in methanol (20 ml). After cooling, the reaction mixture was acidified with 10% HCl and extracted with ethyl acetate (3×15 ml). The combined organic phases were washed with water (2×10 ml), dried over anhydrous sodium sulfate and evaporated under reduced pressure. The residue was chromatographed on $SiO_2$, eluting with 90:10 $CHCl_3$/MeOH, 0.85 g was obtained (98% of the title acid, m.p. 95°–98° C.; H-NMR ($CDCl_3$) δ: 0.68 (s, C-18 Me, 3H); 3.15–3.55 (m, C-3 CH-OH, 1H); 3.8–4.0 (brs, C-3 CH-OH, 1H). Mass spectrum (50 and V) m/e 404.2–386.7–292.9–230.0–216.1–117.4–83.7.

(e) 3-α-7-ξ-dihydroxy-6-ξ-methyl-5-β-cholan-24-oic acid

The compound obtained in (d) (0.460 g, 1.13 mmol) was dissolved in sec-butanol (15 ml); the mixture was refluxed and added with metal sodium (0.460 g). 2 hours after, the reaction mixture was left to cool, diluted with 5 ml of water, acidified with 37% HCl and extracted with ethyl acetate (3×10 ml). The combined organic fractions were dried over anhydrous sodium sulfate and evaporated under reduced pressure. The residue was purified on $SiO_2$ (φ 2.5, h 18). By elution with 98:2 $CHCl_3$/Me OH, 0.200 g of the acid I (44%) was obtained. m.p. 128°–132° C. H-NMR ($CDCl_3$-$CD_3$OD) δ: 0.7 (s, C-18 Me, 3H); 1.00 (t, C-19 and C-6 Me, 6H); 3.45–3.80 (m, C-3 CH-OH, 1H).

We claim:

1. 3-α-7-dihydroxy-6-methyl-5-β-cholan-24-oic acid.

2. 3-α-7-12-α-trihydroxy-6-methyl-5-β-cholan-24-oic acid.

3. A compound of formula I

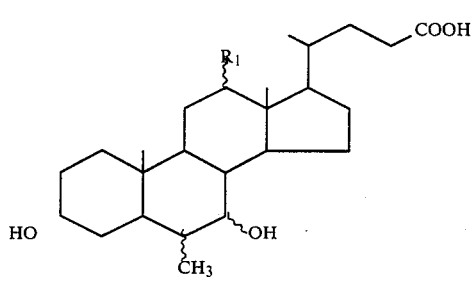

(I)

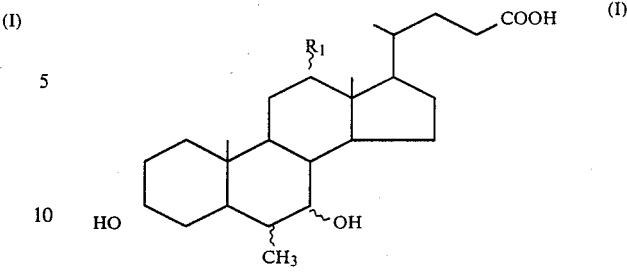

(I)

wherein $R_1$ is hydrogen or hydroxy, and the methyl and hydroxy groups in the 6- and 7-positions respectively are either in α or β configuration.

4. A pharmaceutical composition in unit dosage form having antidyspeptic, eupeptic, antidyslipidemic and choleretic activities containing as the active ingredient 50–500 mgs of a compound of formula I wherein:
$R_1$ is hydrogen or hydroxy, and the methyl and hydroxy groups in the 6- and 7-positions respectively are either in α or β configuration and pharmaceutically acceptable excipients.

5. The composition according to claim 4 in the form of capsules, tablets, dragees, sugar-coated pills, syrups, granulates, or solutions.

* * * * *